United States Patent [19]

Cerri et al.

[11] Patent Number: 5,599,806
[45] Date of Patent: Feb. 4, 1997

[54] HYDRAZINO AND HYDROXYAMINO-14-β-HYDROXYANDROSTANE DERIVATIVES ACTIVE ON THE CARDIOVASCULAR SYSTEM PROCESSES FOR THEIR PREPARATION AND PHARMACEUTICAL COMPOSITIONS CONTAINING SAME

[75] Inventors: Alberto Cerri, Gessate; Giuseppe Bianchi, Milan; Patrizia Ferrari, Varese; Elena Folpini, Milan; Piero Melloni, Bresso, all of Italy

[73] Assignee: Sigma-Tau Industrie Farmaceutiche Riunite S.p.A., Rome, Italy

[21] Appl. No.: 444,366

[22] Filed: May 18, 1995

[30] Foreign Application Priority Data

Jun. 13, 1994 [DE] Germany ............... 44 20 501.5

[51] Int. Cl.⁶ ................ A61K 31/58
[52] U.S. Cl. ........... 514/174; 514/176; 514/182; 540/106; 540/108; 540/109; 540/112; 540/113; 552/522; 552/540; 552/548; 552/554; 552/563; 552/582; 552/610
[58] Field of Search .................. 552/522, 540, 552/548, 554, 563, 582, 610; 514/182, 174, 176; 540/106, 108, 109, 112, 113

[56] References Cited

U.S. PATENT DOCUMENTS 5,324,719  6/1994  Frigerio et al. .
5,444,055  8/1995  Cerri et al. ............... 514/182

Primary Examiner—Kimberly J. Prior
Attorney, Agent, or Firm—Oblon, Spivak, McClelland, Maier & Neustadt, P.C.

[57] ABSTRACT

The invention describes hydrazino and hydroxyamino-14β-hydroxyandrostane derivatives having general formula (I):

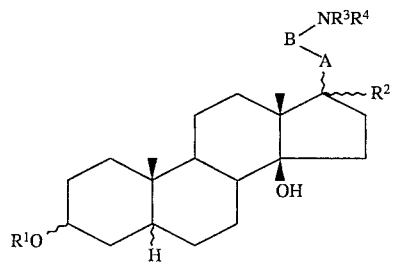

wherein the symbol ～ means α or β configuration and A, B, $R^1$, $R^2$, $R^3$, and $R^4$ have the meanings given in the description and their use in the treatment of cardiovascular disorders such as heart failure and hypertension.

18 Claims, No Drawings

HYDRAZINO AND HYDROXYAMINO-14-β-HYDROXYANDROSTANE DERIVATIVES ACTIVE ON THE CARDIOVASCULAR SYSTEM PROCESSES FOR THEIR PREPARATION AND PHARMACEUTICAL COMPOSITIONS CONTAINING SAME

The present invention relates to new 17-substituted hydrazino-, 17-substituted hydrazinoalkyl-, 17-substituted hydrazinomethylalkenyl-, 17-hydroxyamino-, 17-substituted hydroxyamino-, 17-hydroxyaminoalkyl-, 17-substituted hydroxyaminoalkyl-, 17-hydroxyaminomethylalkenyl and 17-substituted hydroxyaminomethylalkenyl-14β-hydroxyandrostane derivatives active on the cardiovascular system, to a process for their preparation and to pharmaceutical compositions containing same for the treatment of cardiovascular disorders, such as heart failure and hypertension.

The known 17β-guanidinoiminomethyl-5β-androstane-3,β,14β-diol and 17-guanidinoimino-5β-androstane-3β, 14β-diol are reported to be weak inhibitors of $Na^+$, $K^+$-ATPase and weak positive inotropic agents (Gelbart A. and Thomas R., *J. Med. Chem.*, 1978, 21, 284; Schönfeld W. and Repke K., *Quant. Struct.-Act. Relat.*, 1988, 7, 160). Other 17-hydroxyiminomethyl-5β,14β-androstane derivatives (DE 4,227,605; filing date Aug. 20, 1992), hydrazono-5β, 14β-androstane derivatives (DE 4,227,626; filing date Aug. 20, 1992), 17-iminomethylalkenyl- and 17-iminoalkyl-14β-hydroxy-5β-androstane derivatives (DE 4,344,236; filing date Dec. 23, 1993) are reported to inhibit $Na^+$, $K^+$-ATPase. Also N-unsubstituted 17β-aminoalkyl-14β-hydroxy-5β-androstane derivatives (e.g. Templeton J. F. et al., *J. Med. Chem.*, 1993, 36, 42; Templeton J. F. et al., *J. Chem. Soc. Perkin Trans.*, 1992, 2503; Beard N. A. et al., *Br. J. Pharmacol.*, 1975, 54, 65; Boutagy J. and Thomas R., Aust. J. Pharm. Sci., 1973, [NS]2, 9; U.S. Pat. No. 5,144,017-A (publication date Jan. 9, 1992)) and N-unsubstituted 17β-amino-14β-hydroxy-5β-androstane derivatives (e.g. Sch önfeld W. et al., *Biochem. Pharmacol.*, 1986, 35, 3221; DD 235,649-A1 (publication date May 14, 1986)) are known.

The compounds of the present invention have general formula (I):

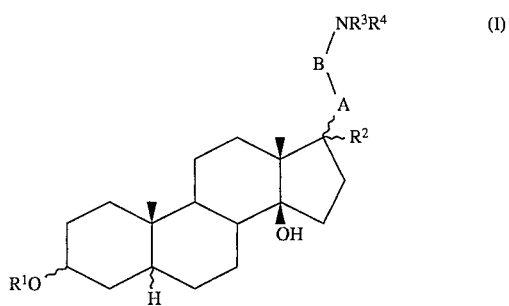

wherein:

the symbol ⁓ means α or β configuration;

A represents $(CH_2)_m$, $-(CH=CH)_n-$ or $-(CH=CCH_3)_n-$;

m represents an integer number from 0 to 4;

n represents an integer number from 0 to 2;

B represents a bond or $CHR^5$ with the proviso that when B represents a bond n=0 and, when $R^2$ is hydroxy, m≠0;

$R^5$ represents hydrogen or methyl;

$R^1$ represents hydrogen, C2–C4 alkyl unsubstituted or substituted by $NR^6R^7$, $NHC(=NH)NH_2$ or OC2–C4 alkoxy unsubstituted or substituted by $NR^6R^7$;

$R^6$, $R^7$ which may be the same or different, represent hydrogen, C1–C4 alkyl or $R^6$ and $R^7$ may form, taken together with the nitrogen atom, a five- or six-membered heterocyclic ring optionally containing one or more further heteroatoms selected from oxygen and nitrogen;

$R^2$ represents hydrogen or hydroxy;

$R^3$ represents hydrogen or methyl;

$R^4$ represents $NHC(=NR^8)NR^9R^{10}$ or $OR^1$;

$R^8$ represents hydrogen, methyl, C2–C4 alkyl, or phenyl, where the C2–C4 alkyl are unsubstituted or substituted by $NR^6R^7$, wherein $R^6$ and $R^7$ have the previously defined meanings;

$R^9$, $R^{10}$ which may be the same or different, represent hydrogen, methyl, C2–C4 alkyl, unsubstituted or substituted by $NR^6R^7$ wherein $R^6$ and $R^7$ have the previously defined meanings;

$R^8$, $R^9$, $R^{10}$ taken two by two may form, together with the heteroatoms they are linked to and where possible, a five- or six- or seven-membered heteromonocyclic ring.

Where the compounds of formula (I) can exhibit tautomerism, the formula is intended to cover all tautomers; the invention encompasses within its scope all the possible stereoisomers, i.e. Z and E isomers, optical isomers and their mixtures, the metabolites and the metabolic precursors of compound formula (I).

Also the pharmaceutically acceptable salts are included in the scope of the invention. Pharmaceutically acceptable salts are salts which retain the biological activity of the base and are derived from such known pharmacologically acceptable acids such as, e.g., hydrochloric, hydrobromic, sulfuric, phosphoric, fumaric, succinic, oxalic, malic, tartaric, maleic, citric, methanesulfonic or benzoic acid and others commonly used in the art.

The compounds of the invention also include solvates (e.g. hydrates).

N-oxides, where the nitrogen atom is not substituted with a hydrogen atom, are also encompassed by the invention.

The alkyl groups are branched or straight chain groups or cyclic groups.

The C2–C4 alkyl is preferably ethyl, n-propyl, iso-propyl, n-butyl or tert-butyl.

The C1–C4 alkyl is preferably methyl, ethyl, n-propyl, iso-propyl, n-butyl, tert-butyl.

The $R^1$ group is preferably hydrogen, methyl, 2-aminoethyl, 3-aminopropyl, 4-aminobutyl, 2-dimethylaminoethyl, 3-dimethylaminopropyl, 4-dimethylaminobutyl, 2-diethylaminoethyl, 3-diethylaminopropyl, 4-dimethylaminobutyl, 2-(1-pyrrolidinyl)ethyl, 3-(1-pyrrolidinyl)propyl, 4-(1-pyrrolidinyl)butyl, 2-guanidinoethyl, 3-guanidinopropyl, 4-guanidinobutyl, 2-(2-dimethylaminoethoxy)ethyl, 2-[2-(1-pyrrolidinyl)ethoxy]ethyl.

The $NR^8$ group is preferably imino, methylimino, ethylimino, iso-propylimino, phenylimino.

The $NR^9R^{10}$ group is preferably amino, methylamino, dimethylamino, diethylamino, iso-propylamino, pyrrolidinyl, piperidyl, morfolino, piperazin-1-yl, 4-methylpiperazin-1-yl, 4-(2-dimethylaminoethyl)piperazin-1-yl, 2-dimethylaminoethylamino, 2-diethylaminoethylamino, (2-dimethylaminoethyl)methylamino, (2-diethylaminoethyl)methylamino, 3-dimethylaminopropylamino, (3-dimethylaminopropyl)methylamino, 2-(1-pyrrolidinyl)ethylamino, 3-(1-pyrrolidinyl)propylamino, (2-(1-pyrrolidinyl)ethyl)methylamino, (3-(1-pyrrolidinyl)propyl)methylamino.

$R^8$ and $R^9$ groups taken together with the heteroatom they are linked to, are preferably 2-imidazolin-2-yl, 1-methyl-2-imidazolin-2-yl, 2-imidazolyl, 2-(1-methyl)imidazolyl, 1,4,5,6-tetrahydro-2-pyrimidinyl, 1-methyl-1,4,5,6-tetrahydro-2-pyrimidinyl.

Preferred examples of specific compounds according to the present invention are

17β-(2-amidino)hydrazino-5β-androstane-3β,14β-diol
17β-[2-(2-imidazolin-2-yl)]hydrazino-5β-androstane-3β,14β-diol
17β-hydroxyamino-5β-androstane-3β,14β-diol
17β-(2-aminoethoxyamino)-5β-androstane-3β,14β-diol
17β-(3-aminopropoxyamino)-5β-androstane-3β,14β-diol
17β-(4-aminobutoxyamino)-5β-androstane-3β,14β-diol
17β-(2-dimethylaminoethoxyamino)-5β-androstane-3β,14β-diol
17β-(3-dimethylaminopropoxyamino)-5β-androstane-3β,14β-diol
17β-(4-dimethylaminobutoxyamino)-5β-androstane-3β,14β-diol
17β-[N-methyl-N-(2-dimethylaminoethoxy)amino]-5β-androstane-3β,14β-diol
17β-[N-methyl-N-(3-dimethylaminopropoxy)amino]-5β-androstane-3β,14β-diol
17β-[N-methyl-N-(4-dimethylaminobutoxy)amino]-5β-androstane-3β,14β-diol
17β-[2-(amidino))]hydrazinomethyl-5β-androstane-3β,14β-diol
17β-[2-(N-methylamidino)]hydrazinomethyl-5β-androstane-3β,14β-diol
17β-[2-(N,N-dimethylamidino)]hydrazinomethyl-5β-androstane-3β,14β-diol
17β-[2-(2-imidazolin-2-yl)]hydrazinomethyl-5β-androstane-3β,14β-diol
17β-[2-(1-methyl-2-imidazolin-2-yl)]hydrazinomethyl-5β-androstane-3β,14β-diol
17β-[2-(1,4,5,6-tetrahydro-2-pyrimidinyl)]hydrazinomethyl-5β-androstane-3β,14β-diol
17β-{2-[N-(2-dimethylaminoethyl)amidino]}hydrazinomethyl-5β-androstane-3β,14β-diol
17β-[2-(N-phenylamidino)]hydrazinomethyl-5β-androstane-3β,14β-diol
17β-hydroxyaminomethyl-5β-androstane-3β,14β-diol
17β-methoxyaminomethyl-5β-androstane-3β,14β-diol
17β-(2-aminoethoxyamino)methyl-5β-androstane-3β,14β-diol
17β-(3-aminopropoxyamino)methyl-5β-androstane-3β,14β-diol
17β-(4-aminobutoxyamino)methyl-5β-androstane-3β,14β-diol
17β-(2-dimethylaminoethoxyamino)methyl-5β-androstane-3β,14β-diol
17β-(3-dimethylaminopropoxyamino)methyl-5β-androstane-3β,14β-diol
17β-(4-dimethylaminobutoxyamino)methyl-5β-androstane-3β,14β-diol
17β-[N-methyl-N-(2-dimethylaminoethoxy)amino]methyl-5β-androstane-3β,14β-diol
17β-[N-methyl-N-(3-dimethylaminopropoxy)amino]methyl-5β-androstane-3β,14β-diol
17β-[N-methyl-N-(4-dimethylaminobutoxy)amino]methyl-5β-androstane-3β,14β-diol
17β-(2-guanidinoethoxyamino)methyl-5β-androstane-3β,14β-diol
17β-(3-guanidinopropoxyamino)methyl-5β-androstane-3β,14β-diol
17β-(4-guanidinobutoxyamino)methyl-5β-androstane-3β,14β-diol
20-(2-amidino)hydrazino-5β-pregnane-3β,14β-diol
20-[2-(2-imidazolin-2-yl)]hydrazino-5β-pregnane-3β,14β-diol
20-[2-(1-methyl-2-imidazolin-2-yl)]hydrazino-5β-pregnane-3β,14β-diol
20-[2-(1,4,5,6-tetrahydro-2-pyrimidinyl)]hydrazino-5β-pregnane-3β,14β-diol
20-hydroxyamino-5β-pregnane-3β,14β-diol
20-(2-aminoethoxyamino)-5β-pregnane-3β,14β-diol
20-(3-aminopropoxyamino)-5β-pregnane-3β,14β-diol
20-(4-aminobutoxyamino)-5β-pregnane-3β,14β-diol
20-(2-dimethylaminoethoxyamino)-5β-pregnane-3β,14β-diol
20-(3-dimethylaminopropoxyamino)-5β-pregnane-3β,14β-diol
20-(4-dimethylaminobutoxyamino)-5β-pregnane-3β,14β-diol
20-[N-methyl-N-(2-dimethylaminoethoxy)amino]-5β-pregnane-3β,14β-diol
20-[N-methyl-N-(3-dimethylaminopropoxy)amino]-5β-pregnane-3β,14β-diol
20-[N-methyl-N-(4-dimethylaminobutoxy)amino]-5β-pregnane-3β,14β-diol
20-(2-guanidinoethoxyamino)-5β-pregnane-3β,14β-diol
20-(3-guanidinopropoxyamino)-5β-pregnane-3β,14β-diol
20-(4-guanidinobutoxyamino)-5β-pregnane-3β,14β-diol
21-(2-amidino)hydrazino-5β-pregnane-3β,14β-diol
21-[2-(2-imidazolin-2-yl)]hydrazino-5β-pregnane-3β,14β-diol
21-[2-(1-methyl-2-imidazolin-2-yl)]hydrazino-5β-pregnane-3β,14β-diol
21-[2-(1,4,5,6-tetrahydro-2-pyrimidinyl)]hydrazino-5β-pregnane-3β,14β-diol
21-hydroxyamino-5β-pregnane-3β,14β-diol
21-(2-aminoethoxyamino)-5β-pregnane-3β,14β-diol
21-(3-aminopropoxyamino)-5β-pregnane-3β,14β-diol
21-(4-aminobutoxyamino)-5β-pregnane-3β,14β-diol
21-(2-dimethylaminoethoxyamino)-5β-pregnane-3β,14β-diol
21-(3-dimethylaminopropoxyamino)-5β-pregnane-3β,14β-diol
21-(4-dimethylaminobutoxyamino)-5β-pregnane-3β,14β-diol
21-[N-methyl-N-(2-dimethylaminoethoxy)amino]-5β-pregnane-3β,14β-diol
21-[N-methyl-N-(3-dimethylaminopropoxy)amino]-5β-pregnane-3β,14β-diol
21-[N-methyl-N-(4-dimethylaminobutoxy)amino]-5β-pregnane-3β,14β-diol
21-(2-guanidinoethoxyamino)-5β-pregnane-3β,14β-diol
21-(3-guanidinopropoxyamino)-5β-pregnane-3β,14β-diol
21-(4-guanidinobutoxyamino)-5β-pregnane-3β,14β-diol
17β-[3-(2-amidino)]hydrazinopropyl-5β-androstane-3β,14β-diol
17β-{3-[2-(2-imidazolin-2-yl)]hydrazinopropyl}-5β-androstane-3β,14β-diol
17β-{3-[2-(1-methyl-2-imidazolin-2-yl)]hydrazinopropyl}-5β-androstane-3β,14β-diol
17β-{3-[2-(1,4,5,6-tetrahydro-2-pyrimidinyl)]hydrazinopropyl}-5β-androstane-3β,14β-diol
17β-(3-hydroxyaminopropyl)-5β-androstane-3β,14β-diol
17β-[3-(2-aminoethoxyamino)propyl]-5β-androstane-3β,14β-diol
17β-[3-(3-aminopropoxyamino)propyl]-5β-androstane-3β,14β-diol
17β-[3-(4-aminobutoxyamino)propyl]-5β-androstane-3β,14β-diol 17β-[3-(2-dimethylaminoethoxyamino)propyl]-5β-androstane-3β,14β-diol
17β-[3-(3-dimethylaminopropoxyamino)propyl]-5β-androstane-3β,14β-diol
17β-[3-(4-dimethylaminobutoxyamino)propyl]-5β-androstane-3β,14β-diol
17β-{3-[N-methyl-N-(2-dimethylaminoethoxy)amino]propyl}-5β-androstane-3β,14β-diol
17β-{3-[N-methyl-N-(3-dimethylaminopropoxy)amino]propyl}-5β-androstane-3β,14β-diol
17β-{3-[N-methyl-N-(4-dimethylaminobutoxy)amino]propyl}-5β-androstane-3β,14β-diol
17β-[3-(2-guanidinoethoxyamino)propyl]-5β-androstane-3β,14β-diol
17β-[3-(3-guanidinopropoxyamino)propyl]-5β-androstane-3β,14β-diol
17β-[3-(4-guanidinobutoxyamino)propyl]-5β-androstane-3β,14β-diol
(E)-17β-{3-[2-(amidino)]hydrazino-1-propenyl}-5β-androstane-3β,14β-diol
(E)-17β-{3-[2-(2-imidazolin-2-yl)]hydrazino-1-propenyl}-5β-androstane-3β,14β-diol
(E)-17β-{3-[2-(1-methyl-2-imidazolin-2-yl)]hydrazino-1-propenyl}-5β-androstane-3β,14β-diol
(E)-17β-{3-[2-(1,4,5,6-tetrahydro2-pyrimidinyl)]hydrazino-1-propenyl}-5β-androstane-3β,14β-diol
(E)-17β-(3-hydroxyamino-1-propenyl)-5β-androstane-3β,14β-diol
(E)-17β-[3-(2-aminoethoxyamino)-1-propenyl]-5β-androstane-3β,14β-diol
(E)-17β-[3-(3-aminopropoxyamino)-1-propenyl]-5β-androstane-3β,14β-diol
(E)-17β-[3-(4-aminobutoxyamino)-1-propenyl]-5β-androstane-3β,14β-diol
(E)-17β-[3-(2-dimethylaminoethoxyamino)-1-propenyl]-5β-androstane-3β,14β-diol
(E)-17β-[3-(3-dimethylaminopropoxyamino)-1-propenyl]-5β-androstane-3β,14β-diol
(E)-17β-[3-(4-dimethylaminobutoxyamino)-1-propenyl]-5β-androstane-3β,14β-diol
(E)-17β-{3-[N-methyl-N-(2-dimethylaminoethoxy)amino]-1-propenyl}-5β-androstane-3β,14β-diol
(E)-17β-{3-[N-methyl-N-(3-dimethylaminopropoxy)amino]-1-propenyl}-5β-androstane-3β,14β-diol
(E)-17β-{3-[N-methyl-N-(4-dimethylaminobutoxy)amino]-1-propenyl}-5β-androstane-3β,14β-diol
(E)-17β-[3-(2-guanidinoethoxyamino)-1-propenyl]-5β-androstane-3β,14β-diol
(E)-17β-[3-(3-guanidinopropoxyamino)-1-propenyl]-5β-androstane-3β,14β-diol
(E)-17β-{3-[2-(amidino)]hydrazino-2-methyl-1-propenyl}-5β-androstane-3β,14βdiol
(E)-17β-{3-[2-(2-imidazolin-2-yl)]hydrazino-2-methyl-1-propenyl}-5β-androstane-3β,14βdiol
(E)-17β-{3-[2-(1-methyl-2-imidazolin-2-yl)]hydrazino-2-methyl-1-propenyl}-5β-androstane-3β,14βdiol
(E)-17β-{3-[2-(1,4,5,6-tetrahydro-2-pyrimidinyl)]hydrazino-2-methyl-1-propenyl}-5β-androstane-3β,14βdiol
(E)-17β-3-hydroxyamino-2-methyl-1-propenyl)-5β-androstane-3β,14βdiol
(E)-17β-[3-(2-aminoethoxyamino)-2-methyl-1-propenyl]-5β-androstane-3β,14βdiol
(E)-17β-[3-(3-aminopropoxyamino)-2-methyl-1-propenyl]-5β-androstane-3β,14βdiol
(E)-17β-[3-(4-aminobutoxyamino)-2-methyl-1-propenyl]-5β-androstane-3β,14βdiol
(E)-17β-[3-(2-dimethylaminoethoxyamino)-2-methyl-1-propenyl]-5β-androstane-3β,14βdiol
(E)-17β-[3-(3-dimethylaminopropoxyamino)-2-methyl-1-propenyl]-5β-androstane-3β,14βdiol
(E)-17β-[3-(4-dimethylaminobutoxyamino)-2-methyl-1-propenyl]-5β-androstane-3β,14βdiol
(E)-17β-{3-[N-methyl-N-(2-dimethylaminoethoxy)amino]-2-methyl-1-propenyl}-5β-androstane-3β,14β-diol
(E)-17β-{3-[N-methyl-N-(3-dimethylaminopropoxy)amino]-2-methyl-1-propenyl}-5β-androstane-3β,14β-diol
(E)-17β-{3-[N-methyl-N-(4-dimethylaminobutoxy)amino]-2-methyl-1-propenyl}-5β-androstane-3β,14β-diol
(E)-17β-[3-(2-guanidinoethoxyamino)-2-methyl-1-propenyl]-5β-androstane-3β,14β-diol
(E)-17β-[3-(3-guanidinopropoxyamino)-2-methyl-1-propenyl]-5β-androstane-3β,14β-diol
(E,E)-17β-{5-[2-(amidino)]hydrazino-1,3-pentadienyl}-5β-androstane-3β,14β-diol
(E,E)-17β-{5-[2-(2-imidazolin-2-yl)]hydrazino-1,3-pentadienyl}-5β-androstane-3β,14β-diol
(E,E)-17β-{5-[2-(1,4,5,6-tetrahydro-2-pyrimidinyl)]hydrazino-1,3-pentadienyl}-5β-androstane-3β,14β-diol
(E,E)-17β-(5-hydroxyamino-1,3-pentadienyl)-5β-androstane-3β,14β-diol
(E,E)-17β-[5-(2-aminoethyoxyamino)-1,3-pentadienyl]-5β-androstane-3β,14β-diol
(E,E)-17β-[5-(3-aminopropoxyamino)-1,3-pentadienyl]-5β-androstane-3β,14β-diol
(E,E)-17β-[5-(2-dimethylaminoethyoxyamino)-1,3-pentadienyl]-5β-androstane-3β,14β-diol
(E,E)-17β-[5-(3-dimethylaminopropoxyamino)-1,3-pentadienyl]-5β-androstane-3β,14β-diol
(E,E)-17β-[5-(2-guanidinoethoxyamino)-1,3-pentadienyl]-5β-androstane-3β,14β-diol
(E,E)-17β-[5-(3-guanidinopropoxyamino)-1,3-pentadienyl]-5β-androstane-3β,14β-diol and the corresponding 3β-(2-aminoethyl), 3β-(2-dimethylaminoethyl), 3β-(2-diethylaminoethyl), 3β-[2-(1-pyrrolidinyl)ethyl], 3β-(3-aminopropyl), 3β-(3-dimethylaminopropyl), 3β-(3-diethylaminopropyl), 3β-[3-(1-pyrrolidinyl)propyl], 3β-[2-(2-dimethylaminoethoxy)ethyl], 3β-[3-(2-dimethylaminoethoxy)propyl], 3β-{2-[2-(1-pyrrolidinyl)ethoxy]ethyl}, 3β-{3-[2-(1-pyrrolidinyl)ethoxy]ethyl} ethers of the compounds mentioned above;

and the corresponding 3α-compounds corresponding to the 3β-compounds mentioned above;

and the corresponding 17α-hydroxy compounds of all the compounds mentioned above;

and the corresponding 5α-androstane derivatives of all the 5β-androstane derivatives mentioned above.

The invention furthermore provides a process for the preparation of compounds of general formula (I), which comprises a reduction reaction of compounds of formula (II)

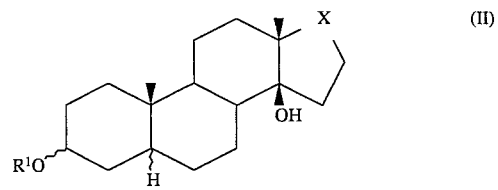

in which $R^1$ and the symbol ⁓ are as above defined and X represents

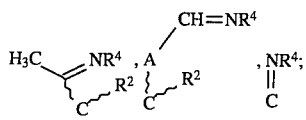

wherein A, $R^2$ and $R^4$ have the meanings above defined, to give compounds of general formula (I).

Compounds (II) can be used as the free base or in the form of a salt with an acid such as, e.g., hydrochloric, hydrobromic, hydroiodic, oxalic, tartaric or sulfuric acid.

The reduction reactions can be carried out using hydrogen in the presence of a catalyst, such as palladium on charcoal, platinum dioxide or Raney Nickel; the catalytic reduction reaction can also be performed in hydrogen transfer conditions using, e.g., ammonium formate or sodium hypophosphite in the presence of one of the above said catalysts. The reduction reaction can also be carried out with metal hydrides such as, e.g., sodium borohydride, sodium cyanoborohydride, borane.

The reduction reactions can be carried out in a solvent, such as ethanol, methanol, acetonitrile, dioxane, tetrahydrofuran, water or a mixture of said solvents, at a temperature between 0° C. and the boiling point of the solvents mentioned above or of their mixtures. To the reaction mixtures, additional acids, e.g., hydrochloric, hydrobromic, sulfuric, acetic, phosphoric acid, and bases such as, e.g., sodium or potassium hydroxide, can be added to maintain the desired pH.

Compounds of general formula (I) can be transformed into other compounds of general formula (I) e.g. by means of one of the methods described herebelow.

Compounds of general formula (I) wherein $R^3$ is methyl and/or $R^6$ and $R^7$ are methyl or ethyl can be obtained from the corresponding compounds of general formula (I) wherein $R^3$, $R^6$ and $R^7$ are hydrogen by alkylation with a methyl halide, ethyl halide, dimethyl sulfate or diethyl sulfate in the presence of a base such as, e.g., sodium hydroxide or potassium carbonate or by reductive alkylation with formaldehyde or acetaldehyde and formic acid or sodium cyanoborohydride.

All said transformations are examples of established procedures described in Organic Chemistry (see for example: J. March "Advanced Organic Chemistry", J. Wiley & Sons, 1985; D. Barton and W. D. Ollis "Comprehensive Organic Chemistry", Pergamon Press, 1979) well known to those skilled in the art.

In all the transformations mentioned above the groups optionally present in $R^4$ are protected, if necessary, by known methods to give, after removal by known methods of protective groups, if any, a compound of general formula (I).

Compounds of general formula (II), wherein the hydrogen in the position 5 is in the β configuration, are prepared according to the methods described in the following German Patent Applications for the same or similar compounds: DE 4,227,605 (filing date Aug. 20, 1992); DE 4,227,626 (filing date Aug. 20, 1992); DE 4,334,236 (filing date Dec. 23, 1993);

Compounds of general formula (II), wherein the hydrogen in the position 5 is in the α configuration, are prepared from compounds of general formula (III)

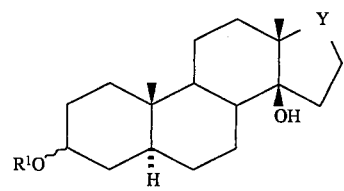

in which
Y represents

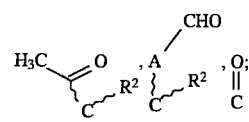

wherein A, $R^1$, $R^2$ and the symbol ⌇ have the meanings above defined, by condensation reaction with compounds of general formula $R^4NH_2$.

The condensation reactions are performed following the methods described in the following German Patent Applications for similar compounds: DE 4,227,605 (filing date Aug. 20, 1992); DE 4,227,626 (filing date Aug. 20, 1992); DE 4,334,236 (filing date Dec. 23, 1993);

Among the compounds of general formula (III), 3β,14β-dihydroxy-5α-androstane-17-one and 3β,14β-dihydroxy-5α-pregnane-20-one are known compounds (Chambers V. E. M. et al, *J. Chem. Soc., Perkin Trans.* 1, 1975, 1, 55; Templeton J. F. et al, *Steroids*, 1993, 58, 518). 3β,14β-Dihydroxy-5α-androstane-17β-carboxaldehyde is prepared from the commercially available uzarigenin following the procedure described by Boutagy for the analogous transformation from digitoxigenin to 3β,14β-dihydroxy-5β-androstane-17β-carboxaldehyde (Boutagy J. S. and Thomas R. E., *Aust. J. Chem.*, 1971, 24, 2723). The other compounds of general formula (III) are prepared following the methods described in the following German Patent Applications for the analogous 5β-derivatives; DE 4,227,605 (filing date Aug. 20, 1992); DE 4,227,626 (filing date Aug. 20, 1992); DE 4,334,236 (filing date Dec. 23, 1993);

In all the transformations the groups optionally present are protected, if necessary, by known methods to give, after removal by known methods of protective groups, if any, a compound of general formula (III).

Compounds of general formula (I) prepared according to the invention and their pharmaceutically acceptable salts are useful agents for the treatment of cardiovascular disorders such as heart failure and hypertension.

Compounds of general formula (I) prepared according to the invention and their pharmaceutically acceptable salts have better therapeutic index compared to known positive inotropic agents such as ouabain, digitoxin and the compounds reported in DE 4,227,605 and DE 4,227,626.

Moreover said compounds (I) show good affinity for the receptor site of the $Na^+$, $K^+$-ATPase.

To test the affinity for the receptor site of the $Na^+$, $K^+$-ATPase and the inhibition of the activity of the enzyme, the following tests were used:

a) displacement of the specific $^3H$-ouabain binding from the $Na^+$, $K^+$-ATPase receptor purified according to Jorghensen (Jorghensen P., *BBA*, 1974, 356, 36) and Erdmann (Erdmann E. et al., *Arzneim. Forsh.*, 1984, 34, 1314);

b) inhibition of the activity of the purified $Na^+$, $K^+$-ATPase measured as % of hydrolysis of $^{32}P$-ATP in the presence and in the absence of the tested compound (Doucet A. et al., *Am. J. Physiol.*, 1986, 251, F851)

Systolic blood pressure (SBP) and hear rate (HR) were measured, by the tail cuff method, in young prehypertensive male rats (MHS or SHR) strains before the development of hypertension (4 weeks of age) for recording the basal values of SBP. Groups of 7 rats were formed and subdivided in control and treated groups.

The compound, suspended in Methocel 0.5% (w/v), was orally given daily for at least 5 weeks to the treated groups. The control group received only Methocel.

SBP and HR were measured weekly 6 and 24 hrs after treatment. After 5 weeks of treatment, when hypertension was fully developed in the control group (9 weeks of age), washout was started for at least one week, to verify whether the treatment maintained blood pressure low or reestablished the basal values.

The validity of this procedure for detecting an hypotensive activity, had been previously tested for β blockers, which did not produce any hypotensive effect when acutely given to hypertensive rats (SHR), but were effective in preventing the development of hypertension when administered starting from weaning for more than 5 weeks. (Takeda K. et al., Japan J. Pharmacol., 1979, 29, 171; Takeda K. et al. Japan J. Pharmacol., 1982, 32, 283; Richer C. et al. Eur. J. Pharmacol, 1978, 47,393).

The affinity and the inhibitory activity of some compounds in the two tests are shown in the following table:

|  | Binding (−log IC50) $^3$H-Ouab. Displacement | Inhibitory Activity (−log IC50) |
|---|---|---|
| Comp. I-aa | 6.9 | 5.7 |
| Comp. I-ab | 6.6 | 5.5 |
| Comp. I-ac | 6.0 | 5.0 |
| Comp. I-ad | 6.5 | 5.4 |
| Comp. I-ae | 5.4 | 4.5 |
| Comp. I-af | 5.0 | 4.2 |
| Comp. I-ag | 6.5 | 5.2 |
| Comp. I-ah | 5.0 | 4.1 |
| Comp. I-ai | 5.1 | 4.1 |
| Comp. I-aj | 7.2 | 6.0 |
| Comp. I-ak | 6.9 | 5.6 |
| Comp. I-al | 6.2 | 4.8 |
| Comp. I-am | 6.1 | 4.3 |
| Comp. I-an | 5.8 | 4.2 |
| Comp. I-ao | 5.9 | 4.1 |
| Comp. I-ap | 5.0 | 4.0 |
| Comp. I-aq | 6.0 | 4.4 |
| Comp. I-ar | 5.7 | 4.2 |
| Comp. I-as | 6.0 | 4.5 |
| Comp. I-at | 6.7 | 5.0 |
| Comp. I-au | 5.9 | 4.4 |
| Comp. I-av | 5.7 | 4.2 |
| Comp. I-ax | 5.7 | 4.4 |
| Comp. I-ay | 5.8 | 4.4 |
| Comp. I-ba | 5.2 | 4.0 |
| Comp. I-bb | 6.3 | 4.5 |
| Comp. I-bc | 6.1 | 4.4 |
| Comp. I-bd | 6.2 | 4.5 |
| Comp. I-be | 6.0 | 4.3 |

The activity of some new compound in preventing the development of hypertension is shown in the following table:

| EFFECT OF 5 WEEK-TREATMENT IN SPONTANEOUS HYPERTENSIVE RATS (MHS) ON THE DEVELOPMENT OF HYPERTENSION | | | | |
|---|---|---|---|---|
| Compound | RATS | DOSE* mg/Kg/os | SBP mm Hg | HR beats/min. |
| Controls | 7 | Methocel | 170 +/− 5.5 | 378 +/− 12.0 |
| Comp. I-aj | 7 | 0.1 | 150 +/− 4.1 | 372 +/− 11.7 |
| Comp. I-am | 7 | 10 | 149 +/− 4.5 | 370 +/− 14.7 |
| Comp. I-am | 7 | 1 | 152 +/− 5.3 | 365 +/− 10.1 |
| Comp. I-bb | 7 | 10 | 150 +/− 4.2 | 375 +/− 12.1 |
| Comp. I-bb | 7 | 1 | 153 +/− 6.2 | 367 +/− 14.3 |

*in Methocel 0.5% w/v

The following examples illustrate the invention without limiting it.

EXAMPLE 1

17β-[2-(Amidino)]hydrazinomethyl-5β-androstane-3β,14β-diol (I-aa)

A mixture of 0.50 g of (E)-17β-guanidinoiminomethyl-5β-androstane-3β,14β-diol hydrochloride (prepared following the procedure described in DE 4,227,626 for similar compounds) and 0.40 g of platinum dioxide in 25 ml of ethanol was hydrogenated at 4.2 atm and room temperature for 8 hrs under shaking. The mixture was filtered and the solution evaporated under reduced pressure. The residue was crystallized from ethanol/ethyl acetate to give 0.30 g of the title compound (I-aa) as a white solid, hydrochloride.

$^1$H-NMR (300 MHz, DMSO-$d_6$, ppm from TMS); 0.80 (3H, s); 0.85 (3H, s); 2.68 (1H, t); 2.78 (1H, dd); 3.85 (1H, bs).

EXAMPLE 2

17β-[2-(2-Imidazolin-2-yl)]hydrazinomethyl-5β-androstane-3β,14β-diol (I-ab)

The title compound (I-ab) (0.29 g) was obtained as a white solid, hydrobromide, starting from (E) 17β-(2-imidazolin-2-yl)hydrazinomethyl-5β-androstane-3β,14β-diol hydrobromide (0.45 g) (prepared as described in DE 4,227, 626) using the same procedure described in Ex. 1.

$^1$H-NMR (300 MHz, DMSO-$d_6$, ppm from TMS); 0.79 (3H, s); 0.86 (3H, s); 2.68 (1H, t); 2.78 (1H, dd); 3.30 (4H, s), 3.85 (1H, bs).

EXAMPLE 3

17β-[2-(1-Methyl-2-imidazolin-2-yl)]hydrazinomethyl-5β-androstane-3β,14β-diol (I-ac)

The title compound (I-ac) (0.35 g) was obtained as a white solid, hydroiodide, starting from (E)-17β-(1-methyl-2-imidazolin-2-yl)hydrazonomethyl-5β-androstane-3β,14β-diol hydroiodide (0.55 g) (prepared as described in DE 4,227, 626) using the same procedure described in Ex. 1.

$^1$H-NMR (300 MHz, DMSO-$d_6$, ppm from TMS); 0.80 (3H, s); 0.85 (3H, s); 2.70 (1H, t); 2.80 (1H, dd); 3.10 (3H, s), 3.65 (4H, s); 3.90 (1H, bs).

EXAMPLE 4

17β-[2-(1,4,5,6-Tetrahydro-2-pyrimidinyl)]-hydrazinomethyl-5β-androstane-3β,14β-diol (I-ad)

The title compound (I-ad) (0.32 g) was obtained as a white solid, hydroiodide, starting from (E)-17β-(1,4,5,6-tetrahydro-2-pyrimidinyl)hydrazonomethyl-5β-androstane-3β,14β-diol hydroiodide (0.60 g) (prepared as described in DE 4,227,626) using the same procedure described in Ex. 1.

$^1$H-NMR (300 MHz, DMSO-$d_6$, ppm from TMS); 0.80 (3H, s); 0.85 (3H, s); 2.70 (1H, t); 2.80 (1H, dd); 3.25 (4H, m), 3.85 (1H, bs).

EXAMPLE 5

17β-{2-[N-(2-Dimethylaminoethyl)amidino]}-hydrazinomethyl-5β-androstane-3β,14β-diol (I-ae)

The title compound (I-ae) (0.38 g) was obtained as a white solid, hydroiodide, starting from (E)-17β-(3-(2-dimethylaminoethyl)guanidinoimino)methyl-5β-androstane-3β,14β-diol hydroiodide (0.55 g) (prepared as described in DE 4,227,626) using the same procedure described in Ex. 1.

$^1$H-NMR (300 MHz, DMSO-$d_6$, ppm from TMS); 0.81 (3H, s); 0.85 (3H, s); 2.65 (1H, t); 2.75 (1H, dd); 2.80 (6H, s); 3.20 (2H, m), 3.60 (2H, m); 3.87 (1H, bs).

EXAMPLE 6

17β-[2-(N-Phenylamidino)]hydrazinomethyl-5β-androstane-3β,14β-diol (I-af)

The title compound (I-af) (0.37 g) was obtained as a white solid, hydrochloride, starting from (E)-17β-(3-phenylguanidino)iminomethyl-5β-androstane-3β,14β-diol (0.55 g) (prepared as described in DE 4,227,626) and adding the stoichiometric amount of hydrochloric acid to the etanolic mixture, using the same procedure described in Ex. 1.

$^1$H-NMR (300 MHz, DMSO-$d_6$, ppm from TMS); 0.85 (3H, s); 0.87 (3H, s); 2.70 (1H, t); 2.80 (1H, dd); 3.85 (1H, bs); 7.00 (1H, m); 7.30 (2H, m); 7.60 (2H, m).

EXAMPLE 7

20-(2-Amidino)hydrazino-5β-pregnane-3β,14β-diol (I-ag)

The title compound (I-ag) (0.38 g) was obtained as a white solid, hydrochloride, starting from (E)-20-guanidinoimino-5β-pregnane-3β,14β-diol (0.65 g) (prepared as described in DE 4,227,626) using the same procedure described in Ex. 6.

$^1$H-NMR (300 MHz, DMSO-$d_6$, ppm from TMS); 0.80 (3H, s); 0.85 (3H, s); 1.50 (3H, bs); 2.70–2.80 (1H, m); 3.85 (1H, bs).

EXAMPLE 8

17β-Hydroxyaminomethyl-5β-androstane-3β,14β-diol (I-ah)

A stirred solution of 0.60 g of (E)-17β-hydroxyiminomethyl-5β-androstane-3β,14β-diol (prepared following the procedure described in DE 4,227,605 for similar compounds) in 6 ml of methanol was acidified to pH 3 with 1N HCl. 0.30 g of NaBH$_3$CN were added and 0.1N HCl was continuously added, by means of a pH-stat, to maintain pH 2.8÷3.0. After 6 hr, 0.15 g of NaBH$_3$CN were added and the reaction was left on stirring overnight. The solution was basified to pH 10 with 2.5N NaOH and methanol was evaporated under reduced pressure. The mixture was extracted with ethyl acetate; the organic layer was dried over anhydrous sodium sulfate and evaporated to dryness under reduced pressure. The residue was purified by flash-chromatography (SiO$_2$) using cyclohexane/ethyl acetate 20/80 as the eluant; the fractions containing the title compound were collected and evaporated to dryness under reduced pressure. The residue was dissolved with diethyl ether/ethyl acetate and the solution was added with the stoichiometric amount of oxalic acid to give 0.45 g of the title compound (I-ah), as a white solid, oxalate.

$^1$H-NMR (300 MHz, CD$_3$OD, ppm from TMS); 0.97 (3H, s); 0.98 (3H, s); 3.25–3.35 (2H, m); 4.05 (1H, bs).

EXAMPLE 9

17β-Methoxyaminomethyl-5β-androstane-3β,14β-diol (I-ai)

The title compound (I-ai) (0.40 g) was obtained as a white solid, oxalate, starting from (E)-17β-methoxyiminomethyl-5β-androstane-3β,14β-diol (0.60 g) (prepared as described in DE 4,227,605) using the same procedure described in Ex. 8.

$^1$H-NMR (300 MHz, CD$_3$OD, ppm from TMS); 0.97 (3H, s); 0.99 (3H, s); 3.25 (1H, dd); 3.33 (1H, dd); 3.80 (3H, s); 4.05 (1H, bs).

EXAMPLE 10

17β-(2-Aminoethoxyamino)methyl-5β-androstane-3β,14β-diol (I-aj)

The title compound (I-aj) (0.23 g) was obtained as a white solid, dihydrochloride, starting from (E)-17β-(2-aminoethoxyamino)methyl-5β-androstane-3β,14β-diol (0.40 g) (prepared as described in DE 4,227,605) following the same procedure described in Ex. 8, but using chloroform/methanol/26% aqueous ammonium hydroxide 90/9/1 as the eluant and hydrochloric acid in an ethanolic solution as the salifying agent.

$^1$H-NMR (300 MHz, CD$_3$OD, ppm from TMS); 0.98 (3H, s); 1.00 (3H, s); 3.33 (2H, m); 3.40–3.55 (2H, m); 4.05 (1H, m); 4.42 (2H, t).

EXAMPLE 11

17β-(3-Aminopropoxyamino)methyl-5β-androstane-3β,14β-diol (I-ak)

The title compound (I-ak) (0.23 g) was obtained as a white solid, dihydrochloride, starting from (E)-17β-(3-aminopropoxyamino)methyl-5β-androstane-3β,14β-diol (0.45 g) (prepared as described in DE 4,227,605) using the same procedure described in Ex. 10.

$^1$H-NMR (300 MHz, CD$_3$OD, ppm from TMS); 0.98 (3H, s); 1.00 (3H, s); 3.15 (2H, m); 3.40–3.55 (2H, m); 4.05 (1H, m); 4.20 (2H, t).

EXAMPLE 12

17β-(4-Aminobutoxyamino)methyl-5β-androstane-3β,14β-diol (I-al)

The title compound (I-al) (0.25 g) was obtained as a white solid, dihydrochloride, starting from (E)-17β-(4-aminobutoxyamino)methyl-5β-androstane-3β,14β-diol (0.35 g) (prepared following the procedure described in DE 4,227,605) using the same procedure described in Ex. 10.

$^1$H-NMR (300 MHz, CD$_3$OD, ppm from TMS); 0.98 (3H, s); 1.00 (3H, s); 3.05 (2H, m); 3.40–3.55 (2H, m); 4.05 (3H, m).

EXAMPLE 13

17β-(2-Dimethylaminoethoxyamino)methyl-5β-androstane-3β,14β-diol (I-am)

The title compound (I-am) (1.37 g) was obtained as a white solid, dihydrochloride, starting from (E)-17β-(2-dimethylaminoethoxyimino)methyl-5β-androstane-3β,14β-diol (1.70 g) (prepared as described in DE 4,227,605) using the same procedure described in Ex. 10.

$^1$H-NMR (300 MHz, CD$_3$OD, ppm from TMS); 0.98 (3H, s); 0.99 (3H, s); 2.99 (6H, s); 3.40–3.55 (2H, m); 3.57 (2H, t); 4.05 (1H, m); 4.53 (2H, t).

EXAMPLE 14

17β-(3-Dimethylaminopropoxyamino)methyl-5β-androstane-3β,14β-diol (I-an)

The title compound (I-an) (0.37 g) was obtained as a white solid, dihydrochloride, starting from (E)-17β-(3-dimethylaminopropoxyimino)methyl-5β-androstane-3β,14β-diol (0.50 g) (prepared as described in DE 4,227,605) using the same procedure described in Ex. 10.

$^1$H-NMR (300 MHz, CD$_3$OD, ppm from TMS); 0.98 (3H, s); 0.99 (3H, s); 2.97 (6H, s); 3.35 (2H,t); 3.40–3.55 (2H, m); 4.05 (1H, m); 4.20 (2H, t).

EXAMPLE 15

17β-(4-Dimethylaminobutoxyamino)methyl-5β-androstane-3β,14β-diol (I-ao)

The title compound (I-ao) (0.27 g) was obtained as a white solid, dihydrochloride, starting from (E)-17β-(3-dimethylaminopropoxyimino)methyl-5β-androstane-3β,14β-diol (0.48 g) (prepared the procedure described in DE 4,227,605 for similar compounds) using the same procedure described in Ex. 10.

$^1$H-NMR (300 MHz, CD$_3$OD, ppm from TMS); 0.98 (3H, s); 1.00 (3H, s); 2.97 (6H, s); 3.20 (2H,t); 3.40–3.55 (2H, m); 4.05 (1H, m); 4.10 (2H, t).

EXAMPLE 16

17β-[N-Methyl-N-(2-dimethylaminoethoxy)amino]-methyl-5β-androstane-3β,14β-diol (I-ap)

To a stirred solution of 0.41 g of 17β-(2-dimethylaminoethoxyamino)methyl-5β-androstane-3β,14β-diol (I-am) and 1.0 ml of 37% aqueous formaldehyde in 10 ml of acetonitrile 0.20 g of NaBH$_3$CN was added. The reaction was stirred for 28 hr and then diluted with 0.1N hydrochloric acid and extracted with ethyl acetate. The aqueous layer was basified to pH 9.5 with 2.5N NaOH and extracted with ethyl acetate; the organic layer was dried over anhydrous sodium sulfate and evaporated to dryness under reduced pressure. The residue was purified by flash-chromatography (SiO$_2$) using chloroform/methanol/26% aqueous ammonium hydroxide 90/9/1 as the eluant; the fractions containing the title compound were collected and evaporated to dryness under reduced pressure. The residue was dissolved with ethyl acetate and the stoichiometric amount of oxalic acid was added to give 0.33 g of the title compound (I-ap), as a white solid, oxalate.

$^1$H-NMR (300 MHz, CD$_3$OD, ppm from TMS); 0.97 (3H, s); 0.99 (3H, s); 2.60 (3H, s); 2.70–2.90 (2H, m); 2.90 (6H, s); 3.32 (2H, t); 3.95–4.00 (2H, m); 4.05 (1H, m).

EXAMPLE 17

17β-(2-Guanidinoethoxyamino)methyl-5β-androstane-3β,14β-diol (I-aq)

The title compound (I-aq) (0.17 g) was obtained as a white solid, dihydrochloride, starting from (E)-17β-(2-guanidinoethoxyimino)methyl-5β-androstane-3β,14β-diol (0.40 g) (prepared as described in DE 4,227,605) using the same procedure described in Ex. 10.

$^1$H-NMR (300 MHz, CD$_3$OD, ppm from TMS); 0.98 (3H, s); 1.00 (3H, s); 3.30 (2H, m); 3.40–3.55 (2H, m); 4.05 (1H, m); 4.40 (2H, t).

EXAMPLE 18

20β-(2-Dimethylaminoethoxyamino)-5β-pregnane-3β,14β-diol (I-ar)

The title compound (I-ar) (0.23 g) was obtained as a white solid, dihydrochloride, starting from (E)-20β-(2-dimethylaminoethoxyimino)-5β-pregnane-3β,14β-diol (0.41 g) (prepared as described in DE 4,227,605) using the same procedure described in Ex. 10.

$^1$H-NMR (300 MHz, CD$_3$OD, ppm from TMS); 0.98 (3H, s); 0.99 (3H, s); 1.55 (3H, s); 2.99 (6H, s); 3.35–3.55 (2H, m); 3.55 (2H, t); 4.05 (1H, m); 4.50 (2H, t).

EXAMPLE 19

17β-{3-[2-(Amidino)]hydrazino-1-propenyl}-5β-androstane-3β,14β-diol (I-as)

The title compound (I-as) (0.18 g) was obtained as a white solid, dihydrochloride, starting from 17β-{3-[guanidinoimino-1-(E)-propenyl]}-5β-androstane-3β,14β-diol (0.40 g) (prepared as described in DE 4,227,605) using the same procedure described in Ex. 10.

$^1$H-NMR (300 MHz, CD$_3$OD, ppm from TMS); 0.85 (3H, s); 0.95 (3H, s); 3.50 (2H, dd); 4.05 (1H, m); 5.40 (1H, m); 5.6 (1H, dd).

EXAMPLE 20

17β-[3-(2-Aminoethoxyamino)-1-propenyl]-5β-androstane-3β,14β-diol (I-at)

The title compound (I-at) (0.30 g) was obtained as a white foam, starting from 17β-[3-(2-aminoethoxyimino)-1-(E)-propenyl]-5β-androstane-3β,14β-diol (0.50 g) (prepared as described in DE 4,344,236) using the same procedure described in Ex. 10, without the final salification.

¹H-NMR (300 MHz, CDCl₃, ppm from TMS); 0.83 (3H, s); 0.95 (3H, s); 2.65 (2H, t); 3.45 (2H, d); 3.66 (2H, t); 4.10 (1H, bs); 5.30 (1H, dt); 5.55 (1H, dd).

EXAMPLE 21

17β-[3-(2-Dimethylaminoethoxyamino)-1-propenyl]-5β-androstane-3β,14β-diol (I-au)

The title compound (I-au) (0.36 g) was obtained as a white foam, starting from 17β-[3-(2-dimethylaminoethoxyimino)-1-(E)-propenyl]-5β-androstane-3β,14β-diol (0.65 g) (prepared as described in DE 4,344,236) using the same procedure described in Ex. 20.

¹H-NMR (300 MHz, CDCl₃, ppm from TMS); 0.83 (3H, s); 0.95 (3H, s); 2.25 (6H, m); 2.49 (2H, t); 3.47 (2H, d); 3.77 (2H, t); 4.10 (1H, bs); 5.30 (1H, dt); 5.57 (1H, dd).

EXAMPLE 22

17β-[3-(2-Dimethylaminoethoxyamino)-2-methyl-1-propenyl]-5β-androstane-3β,14β-diol (I-av)

The title compound (I-av) (0.22 g) was obtained as a white foam, starting from 17β-[3-(2-dimethylaminoethoxyimino)-2-methyl-1-(E)-propenyl]-5β-androstane-3β,14β-diol (0.37 g) (prepared following the procedure described in DE 4,344,236 for similar compounds) using the same procedure described in Ex. 20.

¹H-NMR (300 MHz, CDCl₃, ppm from TMS); 0.83 (3H, s); 0.95 (3H, s); 1.50 (3H, s); 2.25 (6H, m); 2.50 (2H, t); 3.45 (2H, m); 3.75 (2H, t); 4.10 (1H, bs); 5.30 (1H, m).

EXAMPLE 23

(E,E)-17β-[5-(2-Dimethylaminoethoxyamino)-1,3-pentadienyl]-5β-androstane-3β,14β-diol (I-aw)

The title compound (I-aw) (0.28 g) was obtained as a white foam, starting from 17β-[5-(2-dimethylaminoethoxyimino)-(E,E)-1,3-pentadienyl]-5β-androstane-3β,14β-diol (0.42 g) (prepared as described in DE 4,344,236) using the same procedure described in Ex. 20.

¹H-NMR (300 MHz, CDCl₃, ppm from TMS); 0.83 (3H, s); 0.95 (3H, s); 2.25 (6H, m); 2.50 (2H, t); 3.50 (2H, d); 3.75 (2H, t); 4.10 (1H, bs); 5.20–5.70 (4H, m).

EXAMPLE 24

17β-[2-(2-Dimethylaminoethoxyamino)ethyl]-5β-androstane-3β,14β-diol (I-ax)

The title compound (I-ax) (0.24 g) was obtained as a white solid, dihydrochloride, starting from 17β-[2-(2-dimethylaminoethoxyimino)ethyl]-5β-androstane-3β,14β-diol (0.32 g) (prepared as described in DE 4,344,236) using the same procedure described in Ex. 10.

¹H-NMR (300 MHz, CD₃OD, ppm from TMS); 0.98 (3H, s); 1.00 (3H, s); 3.00 (6H, s); 3.35–3.50 (2H, m); 3.55 (2H, t); 4.05 (1H, m); 4.55 (2H, t).

EXAMPLE 25

17β-[3-(2-Dimethylaminoethoxyamino)propyl]-5β-androstane-3β,14β-diol (I-ay)

The title compound (I-ay) (0.32 g) was obtained as a white solid, dihydrochloride, starting from 17β-[2-(2-dimethylaminoethoxyimino)propyl]-5β-androstane-3β,14β-diol (0.47 g) (prepared as described in DE 4,344,236) using the same procedure described in Ex. 10.

¹H-NMR (300 MHz, CD₃OD, ppm from TMS); 0.97 (3H, s); 1.00 (3H, s); 2.99 (6H, s); 3.35–3.50 (2H, m); 3.55 (2H, t); 4.05 (1H, m); 4.55 (2H, t).

EXAMPLE 26

17β-(2-Dimethylaminoethoxyamino)-5β-androstane-3β,14β-diol (I-az)

The title compound (I-az) (0.12 g) was obtained as a white solid, dihydrochloride, starting from 17β-(2-dimethylaminoethoxyimino)-5β-androstane-3β,14β-diol (0.40 g) (prepared as described in DE 4,227,626 for similar compounds) using the same procedure described in Ex. 10.

¹H-NMR (300 MHz, CD₃OD, ppm from TMS); 0.98 (3H, s); 1.10 (3H, s); 3.00 (6H, s); 3.55 (2H, t); 3.60–3.75 (2H, m); 4.05 (1H, m); 4.50 (2H, t).

EXAMPLE 27

17β-(2-Dimethylaminoethoxyamino)methyl-5β-androstane-3β,14β,17α-diol (I-ba)

The title compound (I-ba) (0.17 g) was obtained as a white solid, dihydrochloride, starting from (E)-17β-(2-dimethylaminoethoxyimino)methyl-5β-androstane-3β,14β,17α-diol (0.38 g) (prepared as described in DE 4,227,605) using the same procedure described in Ex. 10.

¹H-NMR (300 MHz, CD₃OD, ppm from TMS); 0.98 (3H, s); 1.00 (3H, s); 3.00 (6H, s); 3.50–3.65 (2H, m); 3.60 (2H, t); 4.05 (1H, m); 4.55 (2H, t).

EXAMPLE 28

3β-(3-Aminopropoxy)-17β-(2-dimethylaminoethoxyamino)methyl-5β-androstane-14β-ol (I-bb)

The title compound (I-bb) (0.20 g) was obtained as a white solid, starting from 3β-(3-aminopropoxy)-17β-(2-dimethylaminoethoxyimino)methyl-5β-androstane-14β-ol (0.44 g) (prepared as described in DE 4,227,605) using the same procedure described in Ex. 20.

¹H-NMR (300 MHz, CD₃OD, ppm from TMS); 0.95 (3H, s); 0.97 (3H, s); 2.25 (2H, t); 2.30 (6H, s); 2.55 (2H, t); 2.90–3.10 (4H, m); 3.70 (1H, m); 3.80 (2H, t).

EXAMPLE 29

3β-(2-Aminoethoxy)-17β-(2-dimethylaminoethoxyamino)methyl-5β-androstane-14β-ol (I-bc)

The title compound (I-bc) (0.18 g) was obtained as a white solid, starting from 3β-(2-aminoethoxy)-17β-(2-dimethylaminoethoxyimino)methyl-5β-androstane-14β-ol (0.43 g) (prepared as described in DE 4,227,605) using the same procedure described in Ex. 20.

¹H-NMR (300 MHz, CD₃OD, ppm from TMS); 0.95 (3H, s); 0.97 (3H, s); 2.30 (6H, s); 2.35 (2H, t); 2.55 (2H, t); 2.90 (1H, dd); 3.10 (1H, dd); 3.60 (1H, m); 3.80 (2H, t).

EXAMPLE 30

3β-[2-(1-Pyrrolidinyl)ethoxy]-17β-(2-dimethylaminoethoxyamino)methyl-5β-androstane-3β,14β-diol (I-bd)

The title compound (I-bd) (0.17 g) was obtained as a white foam, starting from 3β-[2-(2-pyrrolidinyl)ethoxy]-17β-(2-dimethylaminoethoxyimino)methyl-5β-androstane-3β,14β-diol (0.48 g) (prepared as described in DE 4,227,605) using the same procedure described in Ex. 20.

$^1$H-NMR (300 MHz, CD$_3$OD, ppm from TMS); 0.95 (3H, s); 0.97 (3H, s); 2.25 (4H, m); 2.30 (6H, s); 2.55 (2H, t); 2.85–3.10 (5H, m); 3.70 (1H, m); 3.80 (2H, t).

EXAMPLE 31

3β-(3-(1-Pyrrolidinyl)propoxy)-17β-(2-dimethylaminoethoxyamino)methyl-5β-androstane-3β,14β-diol (I-be)

The title compound (I-be) (0.22 g) was obtained as a white foam, starting from 3β-[3-(1-pyrrolidinyl)propoxy]-17β-(2-dimethylaminoethoxyimino)methyl- 5β-androstane-3β,14β-diol (0.42 g) (prepared as described in DE 4,227,605) using the same procedure described in Ex. 20.

$^1$H-NMR (300 MHz, CD$_3$OD, ppm from TMS); 0.95 (3H, s); 0.97 (3H, s); 2.15 (6H, m); 2.25 (2H, t); 2.30 (6H, s); 2.55 (2H, t); 2.90 (1H, dd); 3.10 (1H, dd); 3.70 (1H, m); 3.80 (2H, t).

EXAMPLE 32

(E,E)-17β-[3-(2-Dimethylaminoethoxyimino)-1-propenyl]-5β-androstane-3α,14β-diol (I-bf)

The title compound (I-bf) (0.16 g) was obtained as the base, white foam, starting from (E,E)-17β-[3-(2-dimethylaminoethoxyimino)-1-propenyl]-5β-androstane-3α,14β-diol (0.37 g) (prepared as described in DE 4,344,236) using the same procedure described in Ex. 20.

$^1$H-NMR (300 MHz, CDCl$_3$, ppm from TMS); 0.83 (3H, s); 0.95 (3H, s); 2.25 (6H, m); 2.50 (2H, t); 3.47 (2H, d); 3.77 (2H, t); 3.70 (1H, s); 5.30 (1H, dt); 5.55 (1H, dd).

We claim:

1. A 17-substituted hydrazino-, 17-substituted hydrazinoalkyl-, 17-substituted hydrazinomethylalkenyl-, 17-hydroxyamino-, 17-substituted hydroxyamino-, 17-hydroxyaminoalkyl-, 17-substituted hydroxyaminoalkyl-, 17-hydroxyaminomethylalkenyl or 17-substituted hydroxyaminomethylalkenyl-14β-hydroxyandrostane derivative of general formula I:

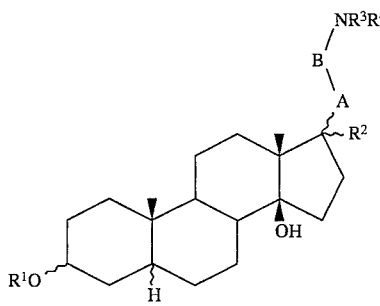

wherein:

the symbol ⌇ means α or β configuration;

A represents (CH$_2$)$_m$, —(CH=CH)$_n$— or —(CH=CCH$_3$)$_n$—;

m represents an integer number from 0 to 4;
n represents an integer number from 0 to 2;

B represents a bond or CHR$^5$;
R$^5$ represents hydrogen or methyl;
R$^1$ represents hydrogen; C2–C4 alkyl unsubstituted or substituted by NR$^6$R$^7$; NHC(=NH)NH$_2$; or C2–C4 alkoxy alkyl unsubstituted or substituted by NR$^6$R$^7$;
R$^6$, R$^7$ which may be the same or different, represent hydrogen, C1–C4 alkyl or R$^6$ and R$^7$ may form, taken together with the nitrogen atom, a five- or six-membered heterocyclic ring optionally containing one or more further heteroatoms selected from oxygen and nitrogen;

R$^2$ represents hydrogen or hydroxy;

R$^3$ represents hydrogen or methyl;

R$^4$ represents NHC(=NR$^8$)NR$^9$R$^{10}$ or OR$^1$;
R$^8$ represents hydrogen, methyl, C2–C4 alkyl, or phenyl, where the C2–C4 alkyl is unsubstituted or substituted by NR$^6$R$^7$, wherein R$^6$ and R$^7$ have the previously defined meanings;

R$^9$, R$^{10}$ which may be the same or different, represent hydrogen, methyl, C2–C4 alkyl, unsubstituted or substituted by NR$^6$R$^7$ wherein R$^6$ and R$^7$ have the previously defined meanings; or R$^8$, R$^9$, R$^{10}$ taken two by two may form, together with the heteroatoms they are linked to, a five- or six- or seven-membered heteromonocyclic ring, with the provisos that (1) when B represents a bond, n=0 and, (2) when R$^2$ is hydroxy, m≠0.

2. A stereoisomer, Z and E isomer, tautomer, optical isomer or mixtures thereof and a pharmaceutically acceptable salt of a compound of general formula I of claim 1.

3. A compound according to claim 1, which is selected from:

17β-(2-amidino)hydrazino-5β-androstane-3β,14β-diol
17β-[2-(2-imidazolin-2-yl)]hydrazino-5β-androstane-3β,14β-diol
17β-hydroxyamino-5β-androstane-3β,14β-diol
17β-(2-aminoethoxyamino)-5β-androstane-3β,14β-diol
17β-(3-aminopropoxyamino)-5β-androstane-3β,14β-diol
17β-(4-aminobutoxyamino)-5β-androstane-3β,14β-diol
17β-(2-dimethylaminoethoxyamino)-5β-androstane-3β,14β-diol
17β-(3-dimethylaminopropoxyamino)-5β-androstane-3β,14β-diol
17β-(4-dimethylaminobutoxyamino)-5β-androstane-3β,14β-diol
17β-[N-methyl-N-(2-dimethylaminoethoxy)amino]-5β-androstane-3β,14β-diol
17β-[N-methyl-N-(3-dimethylaminopropoxy)amino]-5β-androstane-3β,14β-diol
17β-[N-methyl-N-(4-dimethylaminobutoxy)amino]-5β-androstane-3β,14β-diol
17β-[2-(amidino))]hydrazinomethyl-5β-androstane-3β,14β-diol
17β-[2-(N-methylamidino)]hydrazinomethyl-5β-androstane-3β,14β-diol
17β-[2-(N,N-dimethylamidino)]hydrazinomethyl-5β-androstane-3β,14β-diol
17β-[2-(2-imidazolin-2-yl)]hydrazinomethyl-5β-androstane-3β,14β-diol
17β-[2-(1-methyl-2-imidazolin-2-yl)]hydrazinomethyl-5β-androstane-3β,14β-diol
17β-[2-(1,4,5,6-tetrahydro-2-pyrimidinyl)]hydrazinomethyl-5β-androstane-3β,14β-diol 17β-{2-[N-(2-dimethylaminoethyl)amidino]}hydrazinomethyl-5β-androstane-3β,14β-diol
17β-[2-(N-phenylamidino)]hydrazinomethyl-5β-androstane-3β,14β-diol
17β-hydroxyaminomethyl-5β-androstane-3β,14β-diol
17β-methoxyaminomethyl-5β-androstane-3β,14β-diol
17β-(2-aminoethoxyamino)methyl-5β-androstane-3β,14β-diol
17β-(3-aminopropoxyamino)methyl-5β-androstane-3β,14β-diol
17β-(4-aminobutoxyamino)methyl-5β-androstane-3β,14β-diol
17β-(2-dimethylaminoethoxyamino)methyl-5β-androstane-3β,14β-diol
17β-(3-dimethylaminopropoxyamino)methyl-5β-androstane-3β,14β-diol
17β-(4-dimethylaminobutoxyamino)methyl-5β-androstane-3β,14β-diol
17β-[N-methyl-N-(2-dimethylaminoethoxy)amino]methyl-5β-androstane-3β,14β-diol
17β-[N-methyl-N-(3-dimethylaminopropoxy)amino]methyl-5β-androstane-3β,14β-diol
17β-[N-methyl-N-(4-dimethylaminobutoxy)amino]methyl-5β-androstane-3β,14β-diol
17β-(2-guanidinoethoxyamino)methyl-5β-androstane-3β,14β-diol
17β-(3-guanidinopropoxyamino)methyl-5β-androstane-3β,14β-diol
17β-(4-guanidinobutoxyamino)methyl-5β-androstane-3β,14β-diol
20-(2-amidino)hydrazino-5β-pregnane-3β,14β-diol
20-[2-(2-imidazolin-2-yl)]hydrazino-5β-pregnane-3β,14β-diol
20-[2-(1-methyl-2-imidazolin-2-yl)]hydrazino-5β-pregnane-3β,14β-diol
20-[2-(1,4,5,6-tetrahydro-2-pyrimidinyl)]hydrazino-5β-pregnane-3β,14β-diol
20-hydroxyamino-5β-pregnane-3β,14β-diol
20-(2-aminoethoxyamino)-5β-pregnane-3β,14β-diol
20-(3-aminopropoxyamino)-5β-pregnane-3β,14β-diol
20-(4-aminobutoxyamino)-5β-pregnane-3β,14β-diol
20-(2-dimethylaminoethoxyamino)-5β-pregnane-3β,14β-diol
20-(3-dimethylaminopropoxyamino)-5β-pregnane-3β,14β-diol
20-(4-dimethylaminobutoxyamino)-5β-pregnane-3β,14β-diol
20-[N-methyl-N-(2-dimethylaminoethoxy)amino]-5β-pregnane-3β,14β-diol
20-[N-methyl-N-(3-dimethylaminopropoxy)amino]-5β-pregnane-3β,14β-diol
20-[N-methyl-N-(4-dimethylaminobutoxy)amino]-5β-pregnane-3β,14β-diol
20-(2-guanidinoethoxyamino)-5β-pregnane-3β,14β-diol
20-(3-guanidinopropoxyamino)-5β-pregnane-3β,14β-diol
20-(4-guanidinobutoxyamino)-5β-pregnane-3β,14β-diol
21-(2-amidino)hydrazino-5β-pregnane-3β,14β-diol
21-[2-(2-imidazolin-2-yl)]hydrazino-5β-pregnane-3β,14β-diol
21-[2-(1-methyl-2-imidazolin-2-yl)]hydrazino-5β-pregnane-3β,14β-diol
21-[2-(1,4,5,6-tetrahydro-2-pyrimidinyl)]hydrazino-5β-pregnane-3β,14β-diol
21-hydroxyamino-5β-pregnane-3β,14β-diol
21-(2-aminoethoxyamino)-5β-pregnane-3β,14β-diol
21-(3-aminopropoxyamino)-5β-pregnane-3β,14β-diol
21-(4-aminobutoxyamino)-5β-pregnane-3β,14β-diol
21-(2-dimethylaminoethoxyamino)-5β-pregnane-3β,14β-diol
21-(3-dimethylaminopropoxyamino)-5β-pregnane-3β,14β-diol
21-(4-dimethylaminobutoxyamino)-5β-pregnane-3β,14β-diol
21-[N-methyl-N-(2-dimethylaminoethoxy)amino]-5β-pregnane-3β,14β-diol
21-[N-methyl-N-(3-dimethylaminopropoxy)amino]-5β-pregnane-3β,14β-diol
21-[N-methyl-N-(4-dimethylaminobutoxy)amino]-5β-pregnane-3β,14β-diol
21-(2-guanidinoethoxyamino)-5β-pregnane-3β,14β-diol
21-(3-guanidinopropoxyamino)-5β-pregnane-3β,14β-diol
21-(4-guanidinobutoxyamino)-5β-pregnane-3β,14β-diol
17β-[3-(2-amidino)]hydrazinopropyl-5β-androstane-3β,14β-diol
17β-{3-[2-(2-imidazolin-2-yl)]hydrazinopropyl}-5β-androstane-3β,14β-diol
17β-{3-[2-(1-methyl-2-imidazolin-2-yl)]hydrazinopropyl}-5β-androstane-3β,14β-diol
17β-{3-[2-(1,4,5,6-tetrahydro-2-pyrimidinyl)]hydrazinopropyl}-5β-androstane-3β,14β-diol
17β-(3-hydroxyaminopropyl)-5β-androstane-3β,14β-diol
17β-[3-(2-aminoethoxyamino)propyl]-5β-androstane-3β,14β-diol
17β-[3-(3-aminopropoxyamino)propyl]-5β-androstane-3β,14β-diol
17β-[3-(4-aminobutoxyamino)propyl]-5β-androstane-3β,14β-diol
17β-[3-(2-dimethylaminoethoxyamino)propyl]-5β-androstane-3β,14β-diol
17β-[3-(3-dimethylaminopropoxyamino)propyl]-5β-androstane-3β,14β-diol
17β-[3-(4-dimethylaminobutoxyamino)propyl]-5β-androstane-3β,14β-diol
17β-{3-[N-methyl-N-(2-dimethylaminoethoxy)amino]propyl}-5β-androstane-3β,14β-diol
17β-{3-[N-methyl-N-(3-dimethylaminopropoxy)amino]propyl}-5β-androstane-3β,14β-diol
17β-{3-[N-methyl-N-(4-dimethylaminobutoxy)amino]propyl}-5β-androstane-3β,14β-diol
17β-[3-(2-guanidinoethoxyamino)propyl]-5β-androstane-3β,14β-diol
17β-[3-(3-guanidinopropoxyamino)propyl]-5β-androstane-3β,14β-diol
17β-[3-(4-guanidinobutoxyamino)propyl]-5β-androstane-3β,14β-diol
(E)-17β-{3-[2-(amidino)]hydrazino-1-propenyl}-5β-androstane-3β,14β-diol
(E)-17β-{3-[2-(2-imidazolin-2-yl)]hydrazino-1-propenyl}-5β-androstane-3β,14β-diol
(E)-17β-{3-[2-(1-methyl-2-imidazolin-2-yl)]hydrazino-1-propenyl}-5β-androstane-3β,14β-diol
(E)-17β-{3-[2-(1,4,5,6-tetrahydro2-pyrimidinyl)]hydrazino-1-propenyl}-5β-androstane-3β,14β-diol
(E)-17β-(3-hydroxyamino-1-propenyl)-5β-androstane-3β,14β-diol
(E)-17β-[3-(2-aminoethoxyamino)-1-propenyl]-5β-androstane-3β,14β-diol
(E)-17β-[3-(3-aminopropoxyamino)-1-propenyl]-5β-androstane-3β,14β-diol
(E)-17β-[3-(4-aminobutoxyamino)-1-propenyl]-5β-androstane-3β,14β-diol
(E)-17β-[3-(2-dimethylaminoethoxyamino)-1-propenyl]-5β-androstane-3β,14β-diol
(E)-17β-[3-(3-dimethylaminopropoxyamino)-1-propenyl]-5β-androstane-3β,14β-diol (E)-17β-[3-(4-dimethylaminobutoxyamino)-1-propenyl]-5β-androstane-3β,14β-diol
(E)-17β-{3-[N-methyl-N-(2-dimethylaminoethoxy)amino]-1-propenyl}-5β-androstane-3β,14β-diol
(E)-17β-{3-[N-methyl-N-(3-dimethylaminopropoxy)amino]-1-propenyl}-5β-androstane-3β,14β-diol
(E)-17β-{3-[N-methyl-N-(4-dimethylaminobutoxy)amino]-1-propenyl}-5β-androstane-3β,14β-diol
(E)-17β-[3-(2-guanidinoethoxyamino)-1-propenyl]-5β-androstane-3β,14β-diol
(E)-17β-[3-(3-guanidinopropoxyamino)-1-propenyl]-5β-androstane-3β,14β-diol
(E)-17β-{3-[2-(amidino)]hydrazino-2-methyl-1-propenyl}-5β-androstane-3β,14βdiol
(E)-17β-{3-[2-(2-imidazolin-2-yl)]hydrazino-2-methyl-1-propenyl}-5β-androstane-3β,14βdiol
(E)-17β-{3-[2-(1-methyl-2-imidazolin-2-yl)]hydrazino-2-methyl-1-propenyl}-5β-androstane-3β,14βdiol
(E)-17β-{3-[2-(1,4,5,6-tetrahydro-2-pyrimidinyl)]hydrazino-2-methyl-1-propenyl}-5β-androstane-3β,14βdiol
(E)-17β-3-hydroxyamino-2-methyl-1-propenyl)-5β-androstane-3β,14βdiol
(E)-17β-[3-(2-aminoethoxyamino)-2-methyl-1-propenyl]-5β-androstane-3β,14βdiol
(E)-17β-[3-(3-aminopropoxyamino)-2-methyl-1-propenyl]-5β-androstane-3β,14βdiol
(E)-17β-[3-(4-aminobutoxyamino)-2-methyl-1-propenyl]-5β-androstane-3β,14βdiol
(E)-17β-[3-(2-dimethylaminoethoxyamino)-2-methyl-1-propenyl]-5β-androstane-3β,14βdiol
(E)-17β-[3-(3-dimethylaminopropoxyamino)-2-methyl-1-propenyl]-5β-androstane-3β,14βdiol
(E)-17β-[3-(4-dimethylaminobutoxyamino)-2-methyl-1-propenyl]-5β-androstane-3β,14βdiol
(E)-17β-{3-[N-methyl-N-(2-dimethylaminoethoxy)amino]-2-methyl-1-propenyl}-5β-androstane-3β,14β-diol
(E)-17β-{3-[N-methyl-N-(3-dimethylaminopropoxy)amino]-2-methyl-1-propenyl}-5β-androstane-3β,14β-diol
(E)-17β-{3-[N-methyl-N-(4-dimethylaminobutoxy)amino]-2-methyl-1-propenyl}-5β-androstane-3β,14β-diol
(E)-17β-[3-(2-guanidinoethoxyamino)-2-methyl-1-propenyl]-5β-androstane-3β,14β-diol
(E)-17β-[3-(3-guanidinopropoxyamino)-2-methyl-1-propenyl]-5β-androstane-3β,14β-diol
(E,E)-17β-{5-[2-(amidino)]hydrazino-1,3-pentadienyl}-5β-androstane-3β,14β-diol
(E,E)-17β-{5-[2-(2-imidazolin-2-yl)]hydrazino-1,3-pentadienyl}-5β-androstane-3β,14β-diol
(E,E)-17β-{5-[2-(1,4,5,6-tetrahydro-2-pyrimidinyl)]hydrazino-1,3-pentadienyl}-5β-androstane-3β,14β-diol
(E,E)-17β-(5-hydroxyamino-1,3-pentadienyl)-5β-androstane-3β,14β-diol
(E,E)-17β-[5-(2-aminoethyoxyamino)-1,3-pentadienyl]-5β-androstane-3β,14β-diol
(E,E)-17β-[5-(3-aminopropoxyamino)-1,3-pentadienyl]-5β-androstane-3β,14β-diol
(E,E)-17β-[5-(2-dimethylaminoethyoxyamino)-1,3-pentadienyl]-5β-androstane-3β,14β-diol
(E,E)-17β-[5-(3-dimethylaminopropoxyamino)-1,3-pentadienyl]-5β-androstane-3β,14β-diol
(E,E)-17β-[5-(2-guanidinoethoxyamino)-1,3-pentadienyl]-5β-androstane-3β,14β-diol
(E,E)-17β-[5-(3-guanidinopropoxyamino)-1,3-pentadienyl]-5β-androstane-3β,14β-diol and the corresponding 3β-(2-aminoethyl), 3β-(2-dimethylaminoethyl), 3β-(2-diethylaminoethyl), 3β-[2-(1-pyrrolidinyl)ethyl], 3β-(3-aminopropyl), 3β-(3-dimethylaminopropyl), 3β-(3-diethylaminopropyl), 3β-[3-(1-pyrrolidinyl)propyl], 3β-[2-(2-dimethylaminoethoxy)ethyl], 3β-[3-(2-dimethylaminoethoxy)propyl], 3β-{2-[2-(1-pyrrolidinyl)ethoxy]ethyl}, 3β-{3-[2-(1-pyrrolidinyl)ethoxy]ethyl} ethers of the compounds mentioned above;

and the corresponding 3α-compounds corresponding to the 3β-compounds mentioned above;

and the corresponding 17α-hydroxy compounds of all the compounds mentioned above;

and the corresponding 5α-androstane derivatives of all the 5β-androstane derivatives mentioned above.

4. A process for the preparation of said derivative of general formula I of claim 1 which comprises reducing a compound of formula (II)

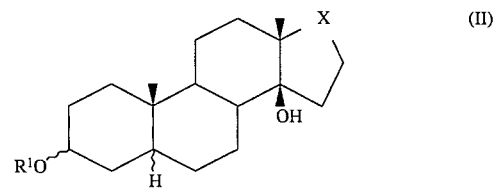

in which $R^1$ and the symbol ～ are as defined in claim 1 and X represents

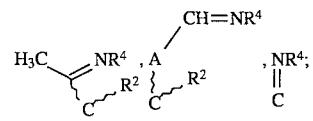

wherein A, $R^2$ and $R^4$ have the meanings defined in claim 1, to give a derivative of general formula I.

5. A pharmaceutical composition containing a compound of general formula I with a pharmaceutically acceptable carrier and/or diluent.

6. A method for the treatment of cardiovascular disorders, heart failure or hypertension which comprises administering to a patient in need thereof an effective amount of a derivative of general formula I as claimed in claim 1.

7. The process according to claim 4, wherein said reducing is carried out using hydrogen in the presence of a catalyst.

8. The process of claim 7, wherein the catalyst is palladium on charcoal, platinum dioxide or Raney Nickel.

9. The process of claim 4, wherein said reducing is carried out using hydrogen transfer conditions.

10. The process of claim 9, wherein the hydrogen transfer conditions comprise using ammonium formate or sodium hypophosphite in the presence of either palladium on charcoal, platinum dioxide or Raney Nickel.

11. The process of claim 4, wherein said reducing is carried out with metal hydrides.

12. The process of claim 11, wherein the metal hydride is selected from the group consisting of sodium borohydride, sodium cyanoborohydride and borane.

13. The process of claim 4, wherein said reducing is carried out in a solvent.

14. The process of claim 13, wherein the solvent is ethanol, methanol, acetonitrile, dioxane, tetrahydrofuran, water, or a mixture thereof.

15. The process of claim 14, wherein said reducing is carried out at a temperature between 0° C. and the boiling point of said solvent or mixture thereof.

16. The process of claim 4, wherein additional acids or bases are added to maintain the desired pH.

17. The process of claim 16, wherein the acid is hydrochloric, hydrobromic, sulfuric, acetic, or phosphoric acid.

18. The process of claim 16, wherein the base is sodium or potassium hydroxide.

* * * * *